United States Patent [19]
Champ

[11] Patent Number: 5,964,739
[45] Date of Patent: Oct. 12, 1999

[54] SAFETY DISPOSABLE NEEDLE STRUCTURE

[76] Inventor: Raynido A. Champ, 4440 Hatton Point Rd., Portsmouth, Va. 23703

[21] Appl. No.: 09/099,735

[22] Filed: Jun. 18, 1998

[51] Int. Cl.⁶ ..................................................... A61M 5/00
[52] U.S. Cl. .......................... 604/263; 604/192; 604/198; 604/411; 604/413; 600/576; 128/919
[58] Field of Search ..................................... 604/263, 274, 604/411, 412, 413, 403, 181, 187, 192, 197, 198; 600/573, 576; 128/919

[56] References Cited

U.S. PATENT DOCUMENTS 4,921,491  5/1990  Champ ..................................... 604/199

Primary Examiner—Ronald Stright
Assistant Examiner—Jeremy Thissell
Attorney, Agent, or Firm—Wallace J. Nelson

[57] ABSTRACT

A disposable needle having individual, spring biased, first and second retractable, open protective sleeves. The first retractable sleeve covers the needle end employed to extract patient blood and the second retractable sleeve covers the needle end that transfers blood to a collection tube. Each sleeve is provided with diametrically disposed slits receiving diametrically disposed ear extensions on the needle support. A support segmented housing maintains the sleeves and needle into a unitary structure. Detents are disposed on the end of the first sleeve that telescopingly receives the open end of the second sleeve. In use, the first sleeve is manually retracted and the detents secure the sleeve in retracted position. A tubular support on the opposite end of the segmented housing receives a blood collection tube therein that forcibly retracts the second sleeve and permit penetration of the blood collection tube. When the blood retraction tube is withdrawn, the second sleeve again provides a protective cover for the needle tip. Upon patient needle removal, the user grasps a pair of arms on the segmented housing and structure thereon removes the detents to permit spring return of the first sleeve to protective needle tip covering status.

10 Claims, 4 Drawing Sheets

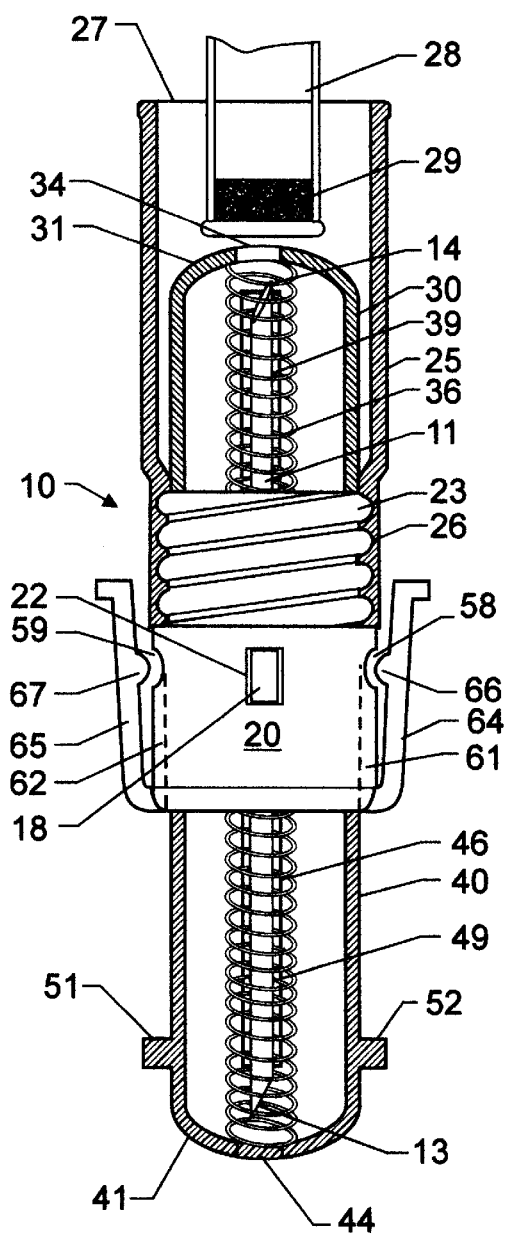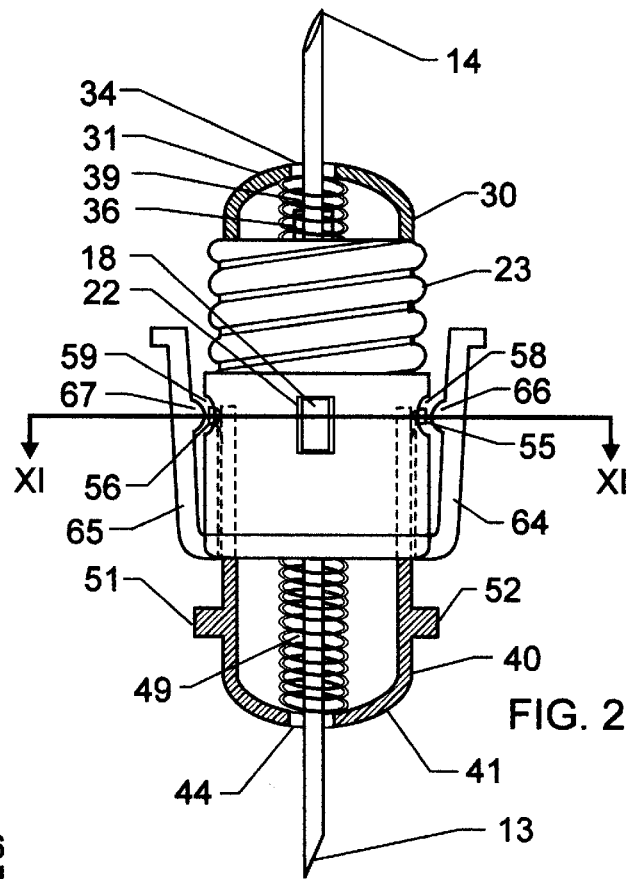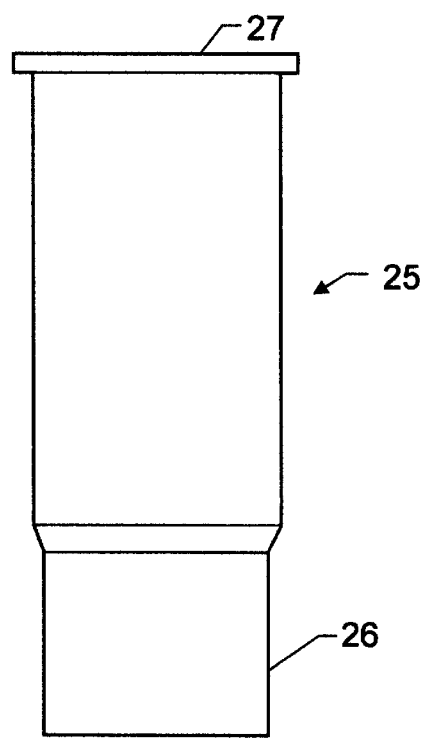
FIG. 1
FIG. 2
FIG. 3

SAFETY DISPOSABLE NEEDLE STRUCTURE

FIELD OF THE INVENTION

This invention relates to disposable needle systems in general and relates specifically to a safety disposable needle system adapted to be contained within a closed protective housing after use to prevent or minimize the chance of human contact with the used sharp needle point(s).

BACKGROUND OF THE INVENTION

Disposable needles and syringes are routinely used in hospitals and other medical facilities for drawing blood and other body fluids from patients, administering medications, and the like. For health and safety reasons, and, as required by law in most jurisdictions, these disposable needles must be properly disposed of after use to prevent inadvertent reuse, accidental injury and possible exposure to transmittable diseases, such as Hepatitis and AIDS. Presently, needles are directly transferred, completely intact and without capping, to collection containers for disposal by incineration, or the like. In all cases, from the time the needle is used, to the time that it is destroyed, medical personnel and clean-up crews are constantly at risk for accidental needle sticks. In the use of these needles, there is always a risk of inadvertent needle stick to the medical personnel handling the device. Once the needle has been deposited into the appropriate collection receptacle, higher risk exists for individuals responsible for ultimate disposal. As the container is filled, exposed needles often protrude through the container opening. Therefore, any individual placing needles in this container risks getting stuck with the contaminated needles.

Traditional needle systems have always been a health hazard risk to our medical personnel. Diseases such as Hepatitis and AIDS have brought to our attention the need to develop devices to better protect our medical personnel from these risks.

Although a number of solutions to this problem have been proposed, there remains a need in the art for a more reliable system to reduce the possibility of inadvertent reuse and safe destruction of disposable needle systems.

U.S. Pat. No. 4,921,491 to Champ, issued May 1, 1990, discloses one such system wherein a separate container of disinfectant is provided for use with each disposable needle. Although this prior art system appears practical and functional in operation, the cost of manufacture, and the inconvenience of using a separate container, have hindered full acceptance thereof at the present time. The present invention employs some of the advantageous features of this prior art system while minimizing the disadvantages thereof.

It is therefore an object of the present invention to provide an improved disposable needle structure to facilitate safe disposal thereof.

Another object of the present invention is a disposable needle system that is simple and inexpensive to manufacture, reliable in operation, and safely disposable to minimize accidental danger to anyone subsequently handling the needle after use.

A further object of the present invention is a new and novel disposable needle structure.

An additional object of the present invention is a disposable needle system that reduces the chance for accidental needle stick injury to the user of the system.

SUMMARY OF THE INVENTION

According to the present invention, the foregoing and additional objects are attained by providing a disposable needle system including an elongated double pointed needle having a circumferentially disposed needle support about an intermediate length thereof. The needle support is provided with a pair of diametrically disposed ears that extend into depressions or sockets in a segmented circumferential housing therefor. One end of the double pointed needle is intended for insertion into the vein of a patient and the other end thereof serves to transfer the patient blood into a collection tube.

A pair of individual, spring biased, retractable sleeves are telescopically disposed about respective ends of the double pointed needle. Each of the pair of retractable sleeves are provided with a first open end and a second rounded end terminating in a smaller diameter opening. Each of the pair of retractable sleeves are also provided with a pair of collinear slits along a portion of the lengths thereof to permit slidable sleeve movement about the ear extensions of the needle support. A spring is disposed abutting each side of the needle support and extends collinear along the length of each needle point to engage the rounded ends and provide a spring force against the ends of the respective retractable sleeves. The retractable sleeve extending over the needle point for insertion into the vein of a patient is provided with a slightly larger outside diameter than that of the sleeve that extends over the needle for transferring the patient blood into a collection to permit telescopic movement between the two sleeves.

The end of the retractable sleeve that extends over the needle point that is inserted into the patient is provided with a pair of diametrically disposed detents on the exterior surface of the open end thereof. When this sleeve is being manually retracted, these detents slidably move along a pair of diametrically disposed grooves provided along the interior surface of the segmented circumferential housing for the needle support where, by their inherent flexible structure, the detents enter diametric through openings in the wall of the segmented housing and lock the slidable sleeve in retracted position to thereby maintain the needle tip previously covered thereby in exposed condition and ready for use.

The sleeve that covers the needle point that transfers patient blood into a collection tube is retracted by the user positioning a blood collection tube thereagainst and exerting sufficient force for the sleeve to retract and the needle to penetrate a rubber septum that closes the blood collection tube. After the blood is received in the collection tube, the tube is removed and the spring force action on this sleeve returns the sleeve to again cover the needle point. Additional blood collection tubes are employed, as needed, until the desired quantity of blood is obtained.

When an adequate quantity of blood has been withdrawn, the other needle point is withdrawn from the patient. A pair of diametrically disposed prongs provided on the exterior of the segmented housing, and in alignment with the detents, are manually squeezed to engage and remove the detents from their lock position and permit the attached sleeve to be moved back over the exposed needle tip that has been removed from the patient, by the action of the spring force acting thereon, and the needle assembly is ready for safe disposal.

BRIEF DESCRIPTION OF THE DRAWINGS

A more complete appreciation of the invention and many of the attendant advantages thereof will be more readily apparent as the same becomes better understood, by reference to the following detailed description, when considered in reference to the accompanying drawings wherein:

FIG. 1 is a schematic view of the disposable needle system of the present invention as appearing in the initial position prior to use and in the final position ready for disposable;

FIG. 2 is a schematic view of the disposable needle system shown in FIG. 1 in position for use, with parts omitted;

FIG. 3 is a schematic view of a blood tube collection tube support as employed in use of the disposable needle system shown in FIGS. 1 and 2;

Figure 4:
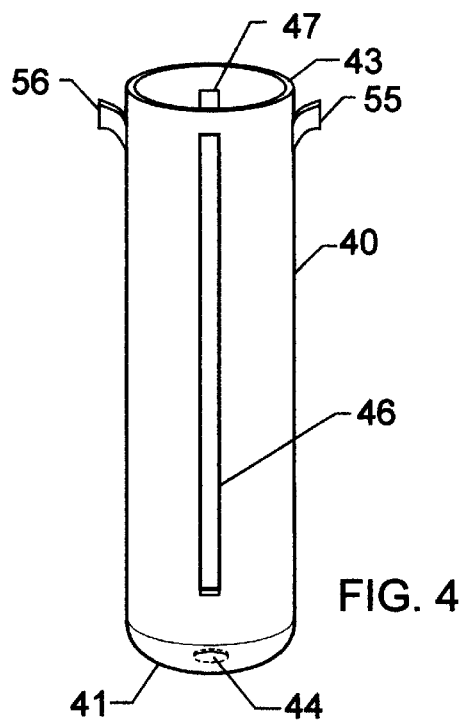
FIG. 4 is a schematic view of one retractable sleeve employed in the construction of the disposable needle system as shown in FIGS. 1 and 2.

Referring now to the drawings, and more particularly to FIGS. 1–3, the disposable needle system of the present invention is shown and designated by reference numeral 10. As shown therein, needle system 10 includes an elongated double end needle 11, formed of stainless steel, or similar material, and having first and second sharp open ends, as designated by reference numerals 13, 14.

Figure 7:
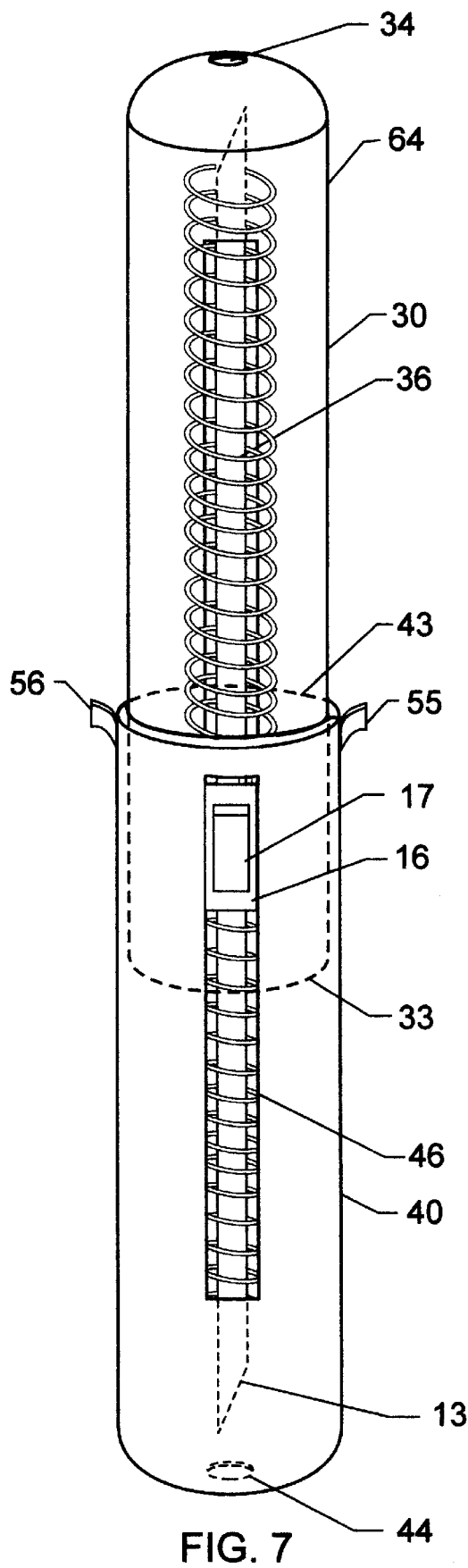
FIG. 7 is a part schematic front view of the needle and support structure as employed in the disposable needle system of the present invention when the telescoped retractable sleeves shown in FIG. 6 are assembled therewith, with parts shown in dotted line and parts omitted.
Figure 8:
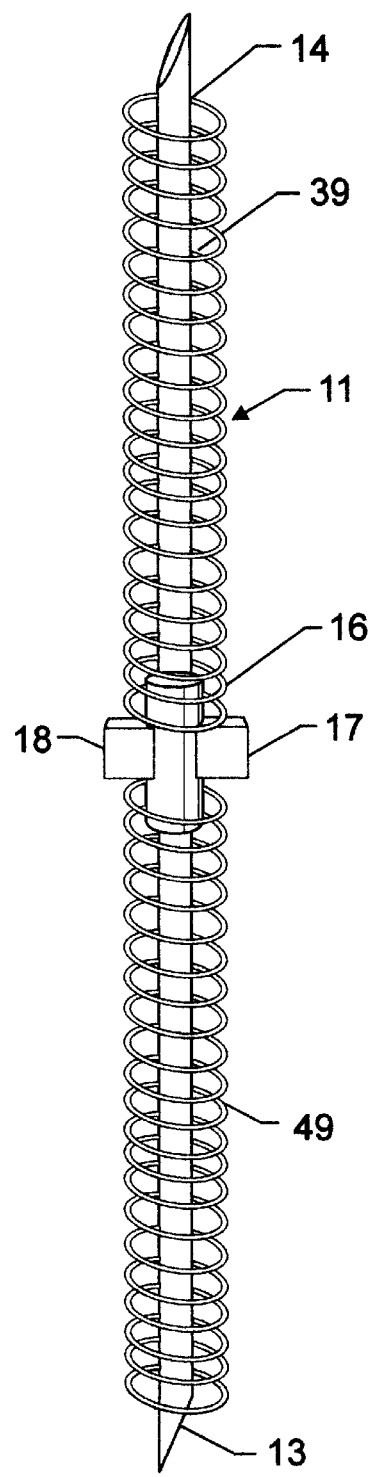
FIG. 8 is a part sectional view of the needle and support structure therefore as seen in the absence of the retractable sleeves and upon ninety degree rotation of the structure from that shown in FIG. 7.

As shown more particularly in FIGS. 7 and 8, a plastic needle support member 16 is fixedly attached to an intermediate length of needle 11. Needle support member 16 is fixed in position by a pair of diametrically opposed integral ear extensions 17,18 within segmented circumferential housing 20, as will be further explained hereinafter.

One ear receiving socket 22 in housing 20 is shown in dotted lines in FIGS. 1 and 2. An elongated, open ended, tubular barrel member 25 (FIG. 3) is provided with an internal threaded section 26 at one end thereof for connection with threaded shank 23 of housing 20.

Figure 5:
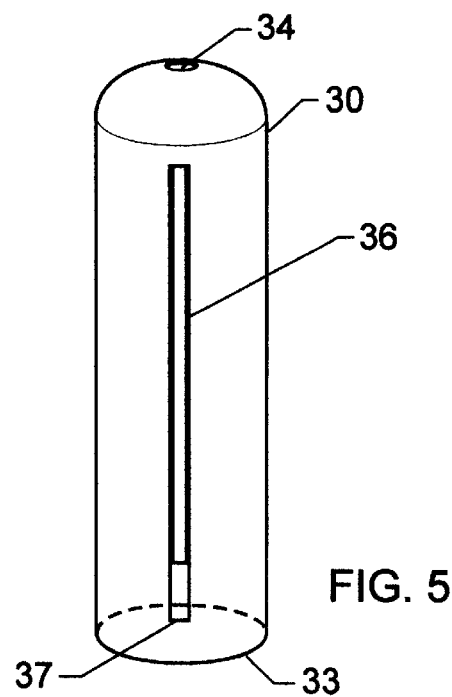
FIG. 5 is a schematic view of the other retractable sleeve employed in the construction of the disposable needle system shown in FIGS. 1 and 2.
Figure 6:
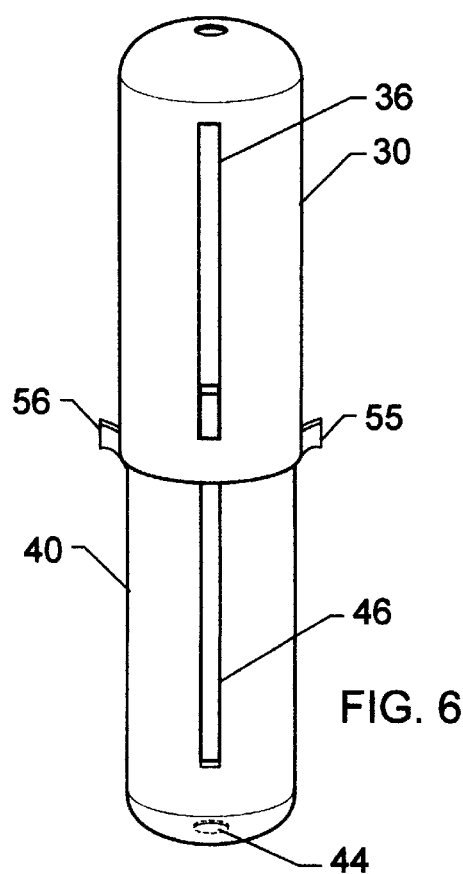
FIG. 6 is a schematic view of the telescoped retractable sleeves shown in FIGS. 4 and 5 with parts omitted for clarity.

The other end 27 of barrel member 25 serves to receive a blood collection tube 28 therein for connection with needle point 14, via rubber septum 29, as will be further explained hereinafter. A first retractable sleeve 30, having a rounded end 31 and an open opposite end 33 (FIGS. 5 and 6), is slidably received within housing 20, and passing through threaded shank 23 of housing 20, as will be further explained hereinafter. Rounded end 31 of sleeve 30 is provided with a central opening 34 therein to permit passage of needle tip 14 therethrough, when first retractable sleeve 30 is telescopically moved to retracted position within housing 20, as will also be further explained hereinafter.

First retractable sleeve 30 is provided with a pair of slits 36 and 37 (FIG. 5) for receipt of ear extensions 17,18 of needle support 16, as will be further explained hereinafter. An elongated first spiral spring 39 is disposed along the length of needle 11 leading to sharp end portion 14 and has one end in engagement with a surface of needle support 16 (FIGS. 7 and 8) and the other end engaging the interior of rounded end 31 of retractable sleeve 30. First spiral spring 39 is provided with a length that normally maintains sleeve 30 in the position shown in FIG. 1. When a retracting force is exerted on the rounded end 31 by blood collecting tube 28 inserted within barrel 25, spring 39 is compressed (FIG. 2) and permits needle point 14 to engage and penetrate the rubber septum 29 of blood collection tube 28. After collecting the blood, blood collecting tube 28 is removed and spiral spring 39 returns sleeve 30 to the position shown in FIG. 1 to cover needle end 14.

A second retractable sleeve 40, having a rounded end 41, and an open opposite end 43, (FIGS. 4 and 6) is also slidably received within housing 20. Rounded end 41 is provided with a central opening 44 therein to permit passage of needle tip 13 therethrough, when second sleeve 40 is moved to retracted position within housing 20. Second retractable sleeve 40 is provided with a pair of slits 46 and 47 (FIG. 4) for engagement with ear extensions 17,18 of needle support 16, as will be further explained hereinafter.

An elongated second spiral spring 49 is disposed along the length of needle portion 13 and has one end in engagement with a surface of needle support 16 (FIGS. 7 and 8) and the other end engaging the interior of rounded end 41 of retractable sleeve 40. Second spiral spring 49 is provided with a length that normally maintains sleeve 40 in the position shown in FIG. 1. When a manual retracting force is exerted on the rounded end 41, by the user grasping diametric extensions 51,52, sleeve 40 is telescopically moved within housing 20 from the safety position shown in FIG. 1 to the locked use position illustrated in FIG. 2.

The locking of sleeve 40 in the position shown in FIG. 2 is achieved by a pair of diametrically opposed resilient detents 55,56 that snap into diametric through openings 58,59 provided in the sidewall of housing 20. Suitable elongated grooves 61,62 (shown in dotted lines in FIGS. 1 and 2) are provided on diametric opposite sides of housing 20 and extend from the through openings thereof to the end of housing 20 that telescopically receives the open end 43 of second sleeve 40.

Grooves 61,62 serve to receive and guide detents 54,55 (FIGS. 2,6, and 12) along the interior of housing 20, as will be further explained hereinafter. A pair of diametrically disposed resilient arms 64,65 have one end attached to the exterior base of housing 20 and an unattached end extending past and in vertical alignment with the openings 58,59 therein. Arms 64,65 are provided with respective rigid, integral, prongs 66,67 extending therefrom, in horizontal alignment with, and directed toward openings 58,59. Upon application of manual pressure against arms 64,65, rigid prongs 66,67 will extend into openings 58,59 and engage and serve to release detents 55, 56 therefrom. Upon release of detents 55,56, spiral spring 49 pushes sleeve 40 from the position shown in FIG. 2 to the position shown in FIG. 1 to thereby again provide a protective covering over the needle end 13.

Figure 10:
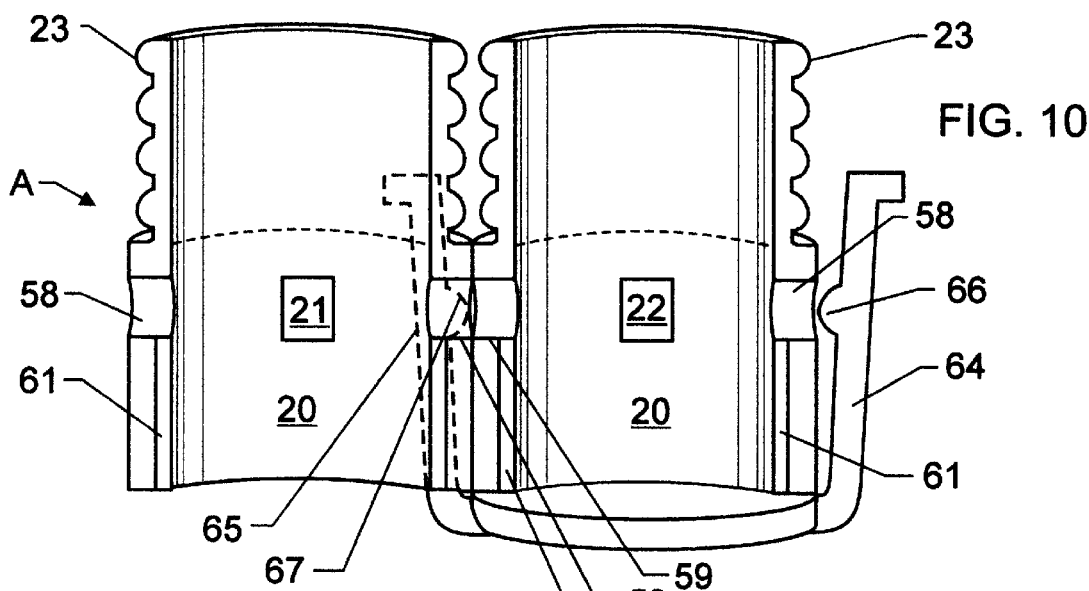
FIG. 10 is a schematic view of the two separate segments employed in the assembly of the needle housing shown in FIG. 9.

Referring more particularly to FIG. 10, the two segments making up circumferential housing 20 are illustrated with one end portion of each segment being shown in engagement with each other.

Figure 9:
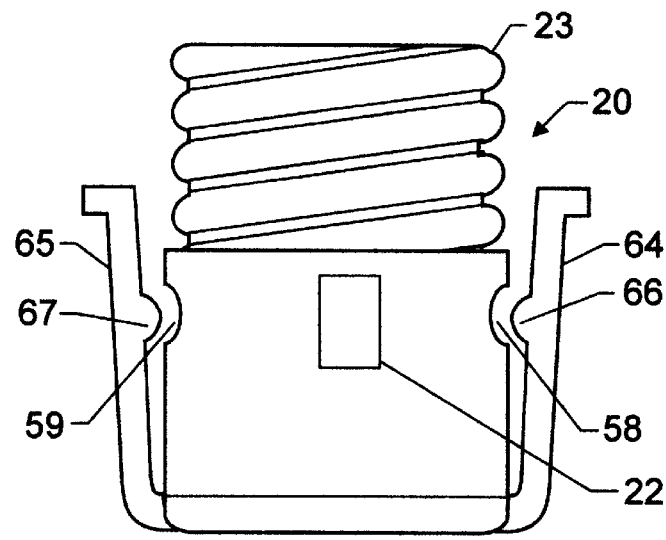
FIG. 9 is a schematic view of the segmented needle housing employed in the disposable system of FIGS. 1 and 2.

In FIG. 9 both ends of each segment are shown in engagement with each other as they are when securing the needle assembly of the present invention in a unitary structure.

Figure 11:
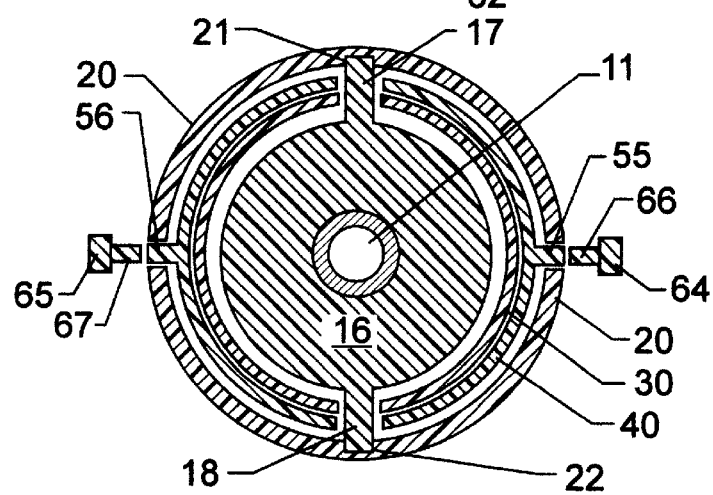
FIG. 11 is a schematic sectional view of the disposable needle system of FIGS. 1 and 2 and as taken along line XI—XI of FIG. 2.

The sectional view of FIG. 11 illustrates the location of ear projections 17 and 18 on needle support 16 maintained in position by engagement with respective depressions or sockets 21,22 on the interior surface of segmented circumferential housing 20. Also, detents 55,56 on sleeve 40 are shown extending through openings 58,59 in housing 20 to lock sleeve 40 in the position shown in FIG. 2. Arms 64,65 with their respective integral prongs 66,67 are illustrated in position to permit manual squeezing thereof to remove detents 55,56 from openings 58,59 and permit spring 49 to again return sleeve 40 over the needle end 13.

Figure 12:
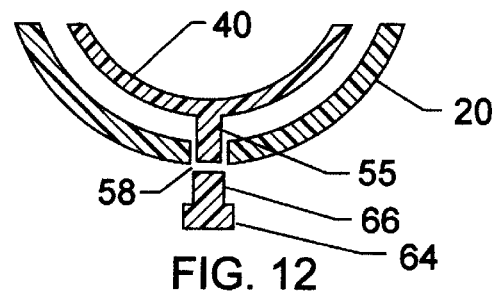
FIG. 12 is an enlarged, part sectional, part schematic view of the release and locking mechanism on one side of the disposable needle system of the present invention, and similar to a portion of FIG. 11.

FIG. 12 is an enlarged partial view of the detent 55 on sleeve 40 and the release mechanism therefor including arm 64 and integral prong 66.

Figure 13:
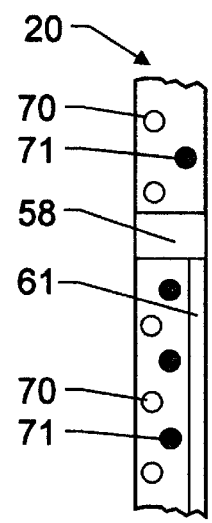
FIG. 13 is an end schematic, partial, view of one side of one of the segments making up the segmented circumferential housing forming part of the disposable needle system of the present invention, as seen looking in the direction of arrow A in FIG. 10, and illustrating the connection features thereof.
Figure 14:
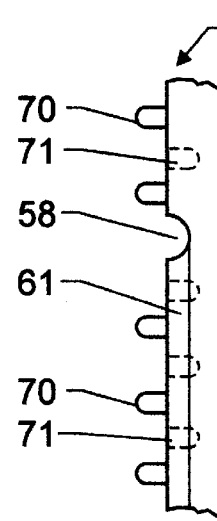
FIG. 14 is a side schematic view of the segment of the circumferential housing shown in FIG. 13.

Referring to FIGS. 13 and 14, the details of the preferred embodiment for securing the segments of housing 20 together is illustrated. As shown therein the open ends of the housing 20 segment are provided with one or more vertical rows of alternate prongs 70 and prong receiving cavities 71. The segment of housing 20 to be joined with that illustrated is provided with alternate prongs and cavities that mate with those shown in the segment illustrated to permit frictional attachment of the segments to form the structure for housing 20 as shown in FIGS. 1, 2 and 9.

The assembly and operation of the present invention is believed apparent from the foregoing description. In assembly, needle 11, with attached needle support 16, is provided with spiral springs 39,49 being disposed in abutting relationship with opposite sides of needle support 16, as shown in FIG. 8.

As illustrated in FIG. 7, sleeve 30 is then slidably positioned over needle point end 14 and forcibly pushed over ears 17, 18 of needle support 16 to place ears 17 and 18 in respective slits 36,37. Spring 39 is of such length as to engage the interior of rounded end 31 of sleeve 30 and one surface of needle support 16. This length of spring 39 maintains sleeve 30 in extended position to cover the end of needle point 14 and maintain ears 17,18 in engagement with the ends of slits 36,37 therein. Sleeve 40 is then slidably positioned over needle point end 13 and the open end 43 thereof telescopically placed over the open end 33 of sleeve 30. Sleeve 40 is then forcibly pushed over ears 17,18 of needle support 16 to place ears 17 and 18 in respective slits 46,47. Spring 49 is of such length as to engage the interior of rounded end 41 of sleeve 40 and one surface of needle support 16. The length of spring 49 maintains sleeve 40 in extended position to cover needle point 13 and maintain ears 17,18 in engagement with the ends of slits 46,47 therein.

The thin construction and the flexibility of the sleeve material permits the forcible positioning of the sleeves over the ears 17,18 while the rigidity of the sleeve material is adequate to maintain the ends of the slits in the respective sleeves in contact with the ears 17 and 18 under the force of the respective springs 39,49. The force of springs 39,49 is adequate to normally maintain the sleeves 30,40 in extended position (FIG. 1) but not sufficient to force the open ends thereof back over ears 17,18.

The structure of FIG. 7 is converted to that shown in FIG. 1 by employing the segmented circumferential housing 20 (FIG. 10) to encircle needle support such that ear extensions 17,18 thereon are received by depressions or sockets 21,22 in the housing segments. The two segments of housing 20 simultaneously align vertical grooves 61,62 therein to receive detents 55,56 of sleeve 40. The segments of housing 20 are secured together by exertion of manual force to frictionally engage prongs 70 within mating prong receiving cavities 71. The assembled structure of FIG. 1 is then ready for sterilization and packaging for subsequent use.

When assembled and ready for use, barrel 25 is threadingly secured to threaded shank 23 of needle system 10. The user grasps diametric extensions 51,52 and manually retracts sleeve 40 into housing 20 to the position shown in FIG. 2, where detents 55,56 engage diametric openings 58,59 in housing 20 to releasably retain sleeve 40 in position with needle point 13 exposed for insertion into a patient's vein. Once inserted into a patient, a suitable blood collection tube 28 is positioned within barrel 25 and, by manual force of the operator, sleeve 30 is telescopically further moved into housing 20 and sleeve 40 to cause needle point 14 to pierce the rubber septum 29 of collection tube 28 and permit the blood from the patient to fill the collection tube.

Once collection tube 28 is filled, it is extracted from sleeve 25 and spiral spring 39 returns sleeve 30 to the position shown in FIG. 1 covering needle point 14. This procedure is repeated until the desired number of collection tubes are filled, and needle point 13 is removed from the vein of the patient.

Arms 64,65 are then manually squeezed toward each other by the needle user, without having to place his hands in front or near the needle point 13. Movement of arms 64,65 toward each other causes prongs 66,67 to engage respective detents 55,56 and remove them from diametric openings 58,59. When the detents 55,56 are removed, compressed spring 49 expands and again moves sleeve 40 to the position shown in FIG. 1 to thereby cover the contaminated needle 13 and needle assembly 10 is ready for disposal in a safe manner.

Although the invention has been described relative to specific embodiments thereof, it is not so limited. There are numerous modifications and variations of the present invention that will be readily apparent to those skilled in the art in the light of the above teachings. For example, no specific materials have been mentioned for construction of the individual components of the present invention, it being understood that the various components of the disposable needle system described herein may be constructed of conventional plastic materials now used for similar systems and including polyethylene, polypropylene, and the like. Detents 55,56 arms 64,65 are conventionally formed integral with and of the same material as that of the component they are attached to. Also needle support 16 may be constructed of a suitable plastics or a hard rubber, if so desired. Needle 11 is constructed of suitable stainless steel, as are spiral springs 39 and 49. Spiral springs may also be composed of suitable plastics allowing recoil strength.

Segmented housing 20 could be formed of other than two segments and the attachment of the segments could be accomplished other than the prong and cavity structure described. In this respect, a suitable shrink sleeve plastic sleeve could be employed around the segmented housing segments in lieu of the prong/cavity attachment described herein.

These and other modifications and variations of the present invention will be readily apparent to those skilled in the art in the light of the above teachings.

It is therefore to be understood that, within the scope of the appended claims, the invention may be practiced other than as specifically described herein.

What is claimed as new and desired to be secured by Letters Patent of the United States is:

1. A disposable needle system for use by an operator in obtaining blood from a patient comprising, in combination:

needle means having a first open end for insertion into the vein of a patient and having a second open end for transferring the patient blood to a collection device;

a needle support member integrally attached to and disposed between the ends of said needle means;

a first retractable sleeve having a first open end and a second rounded end and disposed over said first open end of said needle means with the rounded end thereof being adjacent to, and providing ingress and egress for, said first open end of said needle means;

a second retractable sleeve having an open end and a rounded end and disposed over said second open end of said needle with the rounded end thereof being adjacent to, and providing ingress and egress for, said second open end of said needle means;

first spiral spring means encompassing said first open end of said needle and extending from said rounded end of said first retractable sleeve to said needle support member;

second spiral spring means encompassing said second open end of said needle and extending from said rounded end of said second retractable sleeve to said needle support member;

said open end of said first retractable sleeve telescopically receiving said open end of said second retractable sleeve, a housing surrounding said needle support member and said telescoped open ends of said first and said second retractable sleeves;

means on said first retractable sleeve to facilitate manual retraction thereof against the pressure of said first spiral spring;

detent means disposed on said first retractable sleeve to assist in releasably locking said first retractable in a retracted position;

means on said housing for receiving said detent means when said first retractable sleeve is retracted;

release means carried by said housing to effect release of said detent means from said means on said housing for receiving said detent means; whereby, said first and said second retractable sleeves are movable from a first position wherein they provide a protective cover from the respective first and second open needle ends to a position wherein the first and second needle ends are exposed for use in obtaining and collecting blood from a patient and, after use, said first and said second retractable sleeves are moved back to the first position and thereby reduce the chance of accidental needle sticking of an individual handling and disposing of the used needle system.

2. The disposable needle system of claim 1 including a threaded shank end provided on said housing;

an open barrel threadingly connected to said threaded shank end of said housing;

said open barrel serving as support structure for a blood collection tube positioned therein and against the rounded end of said second retractable sleeve; whereby application of pressure on said second retractable sleeve may be exerted by said blood collection tube to cause said second retractable sleeve to be retracted to expose and permit penetration of said second open end of said needle means into said blood collection tube for collection of blood obtained from the patient via said first open end of said needle means.

3. The disposable needle system of claim 1 wherein said detent means disposed on said first retractable sleeve includes a pair of diametrically disposed detents flexibly extending from the exterior surface, and adjacent the open end, of said first retractable sleeve; and said means on said housing for receiving said detent means is a pair of diametrically disposed openings in said housing.

4. The disposable needle system of claim 3 including guide means disposed within said housing for slidably receiving and controlling the path of movement of said detents while said first retractable sleeve is being retracted.

5. The disposable needle system of claim 4 wherein said guide means comprises a pair of diametrically disposed grooves on the interior surface of said housing, said grooves extending from the end of said housing to said pair of diametrically disposed openings in said housing.

6. The disposable needle system of claim 3 wherein said release means carried by said housing to effect release of said detent means includes a pair of flexible arm extensions connected to and extending from said housing; said pair of flexible arms extensions being vertically aligned with said diametrically disposed openings in said housing for receiving said detent means; each of said pair of flexible arms having an integral prong thereon that is horizontally aligned with said diametrically disposed openings in said housing for receiving said detent means; whereby after use of said disposable needle system for a blood drawing operation, and it is desired to return said first retractable sleeve to a protective covering position over said first open needle end, said pair of flexible arm extensions are manually squeezed toward said housing and said prongs thereon engage and forcibly remove said detents from said housing to permit said first spiral spring to return said first retractable sleeve to again cover said first open needle end to facilitate safe disposable of said needle system.

7. The disposable needle system of claim 1 wherein said needle support member is provided with a pair of diametrically disposed ear extensions and said housing surrounding the needle support member is provided with a pair of diametrically disposed depressions aligned with and serving to receive said pair of diametrically disposed ear extensions of said needle support member.

8. The disposable needle system of claim 7 wherein said housing surrounding the needle support member is formed of two segments and including means for joining said two segments to form said housing.

9. The disposable needle system of claim 8 wherein said means for joining said two segments to form said housing includes a row of alternate prongs and prong receiving cavities disposed on each of the mating surfaces of said two segments.

10. The disposable needle system of claim 7 including a pair of diametrically disposed guide slits provided along the major length of each of said first and said second retractable sleeves; each of said slits in said first and said second retractable sleeves being disposed over one of said diametrically disposed ear extensions of said housing surrounding said needle support member.

* * * * *